(12) United States Patent
Ahern et al.

(10) Patent No.: US 8,562,613 B2
(45) Date of Patent: Oct. 22, 2013

(54) METHOD KIT FOR TREATING BONY DEFECTS

(75) Inventors: James W. Ahern, Austin, TX (US); Arthur Gertzman, Flemington, NJ (US); Karen Roche, Stillwater, MN (US); Moon Hae Sunwoo, Old Tappan, NJ (US); Steven Wolfe, Woodbury, MN (US); Stephen D. Kuslich, Phoenix, AZ (US); John E. Kuslich, legal representative, Phoenix, AZ (US)

(73) Assignees: Spineology Inc., St. Paul, MN (US); Musculoskeletal Transplant Foundation, Edison, NJ (US)

(*) Notice: Subject to any disclaimer, the term of this patent is extended or adjusted under 35 U.S.C. 154(b) by 510 days.

(21) Appl. No.: 12/754,388

(22) Filed: Apr. 5, 2010

(65) Prior Publication Data

US 2010/0286702 A1    Nov. 11, 2010

Related U.S. Application Data

(62) Division of application No. 10/924,240, filed on Aug. 23, 2004, now abandoned.

(60) Provisional application No. 60/497,146, filed on Aug. 22, 2003.

(51) Int. Cl.
*A61F 2/46* (2006.01)

(52) U.S. Cl.
USPC .......................................................... 606/86 R

(58) Field of Classification Search
USPC ............ 606/90, 92–94, 96; 623/17.11–17.16
See application file for complete search history.

(56) References Cited

U.S. PATENT DOCUMENTS

| | | | | |
|---|---|---|---|---|
| 5,989,289 A * | 11/1999 | Coates et al. | | 623/17.16 |
| 6,033,438 A * | 3/2000 | Bianchi et al. | | 623/17.16 |
| 6,096,081 A * | 8/2000 | Grivas et al. | | 623/17.11 |
| 6,224,630 B1 * | 5/2001 | Bao et al. | | 623/17.16 |
| 6,402,784 B1 * | 6/2002 | Wardlaw | | 623/17.11 |
| 6,805,697 B1 * | 10/2004 | Helm et al. | | 606/92 |
| 6,969,404 B2 * | 11/2005 | Ferree | | 623/17.11 |
| 2002/0058947 A1 * | 5/2002 | Hochschuler et al. | | 606/94 |
| 2003/0212426 A1 * | 11/2003 | Olson et al. | | 606/191 |
| 2003/0220649 A1 * | 11/2003 | Bao et al. | | 606/90 |
| 2004/0054414 A1 * | 3/2004 | Trieu et al. | | 623/17.16 |
| 2005/0065609 A1 * | 3/2005 | Wardlaw | | 623/17.12 |
| 2006/0106462 A1 * | 5/2006 | Tsou | | 623/17.16 |

* cited by examiner

*Primary Examiner* — Kevin T Truong
*Assistant Examiner* — Michael Araj
(74) *Attorney, Agent, or Firm* — Skaar Ulbrich Macari, P.A.

(57) ABSTRACT

The present invention is a kit and a method of using a kit for treating bone including a fill material mixture made of osteoconductive material, osteoinductive material and a lubricating carrier, a porous container to receive the fill material mixture and a tool that flowably introduces the fill material mixture into the porous container.

11 Claims, 4 Drawing Sheets

METHOD KIT FOR TREATING BONY DEFECTS

RELATED APPLICATION

This application is a division of application Ser. No. 10/924,240 filed Aug. 23, 2004, which claims the benefit of U.S. Provisional Application No. 60/497,146 filed Aug. 22, 2003, each of which is hereby fully incorporated herein by reference.

FIELD OF INVENTION

The present invention relates generally to the field of materials adapted to replace or assist a component of the skeleton of a living body. More specifically, the present invention relates to a system that surgeons can use for healing and supporting bony defects.

BACKGROUND OF THE INVENTION

Bone grafts are commonly used in a wide variety of orthopedic procedures. In particular, bone graft is often used to aid the healing of bony defects. Such defects may arise from trauma or a pathologic condition, or the surgeon may require graft to support bony healing subsequent to a surgical procedure such as joint fusion or arthrodesis.

Autogenous bone, also called autograft, is generally considered to be the "gold standard" in terms of biological performance. Autograft is often collected from the patient's hip. However, collecting autograft from the patient's hip is associated with a significant incidence of post-operative pain and the potential for additional medical complications. In addition, the volume of autograft material available from the patient's hip may not be sufficient for the graft procedure.

Specially processed donor bone, or allograft, is frequently used as an alternative to autograft. Allograft, such as morselized granules of cortical and cancellous bone, provides an osteoconductive material with some compressive strength, which can be readily incorporated via the same healing process that occurs with autogenous bone. Osteoconductivity refers to a material's ability to provide a suitable structure or scaffold for the growth of new blood vessels and, ultimately, bone.

Allograft which is demineralized during its processing is commonly referred to as DBM, or demineralized bone matrix. DBM is an osteoinductive material, meaning that it can lead to the formation of bone by recruiting mesenchymal stem cells from the surrounding tissues, and these cells can ultimately differentiate into new bone.

The Optimesh® System (patented by Spineology, Inc. in U.S. Pat. Nos. 5,549,679; 5,571,189, 6,383,188; 6,620,162; 6,620,169 and U.S. patent application Ser. Nos. 09/909,667 and 10/440,036 all of which are incorporated herein by reference) includes various tools and a porous container used to contain bone graft or other fill material when fusing intervertebral spaces and treating defects in intravertebral bones or other bones. While the current Optimesh® System utilizes the concept of fill material extrusion, it would be advantageous to capitalize on the characteristics of both the osteoconductive and osteoinductive materials.

SUMMARY OF THE INVENTION

To maximize the benefits of osteoinductive and osteoconductive fill materials, there is a need for carefully selecting and controlling the fill material flow into bony defects. It would be a particularly useful improvement to the Optimesh® System to fill the porous container with a fill material mixture that is filtered, under pressure, by the container such that bone inducing material flows out of the porous container and contacts the surrounding tissue, while the container restrains osteoconductive material in the container to provide support and rigidity to the defect.

The present invention includes a method and apparatus for healing and supporting bony defects. The method and apparatus of the present invention combine the advantageous features of osteoconductive and osteoinductive allograft materials. The present invention capitalizes upon the unique properties of each component by utilizing a mesh container placed in a bony defect. The allograft mixture is injected into the mesh container such that the osteoconductive material provides compressive strength to support the bony defect and the osteoinductive material encourages bone growth to aid in the healing of the bony defect.

The allograft mixture is formulated to be flowable, that is the material may be discharged from a small diameter tube of length significantly longer than the tube's diameter. The allograft mixture is also packable such that the mixture may fill a small mesh container or pouch so that the mesh fills to its geometric limits as it is filled with the allograft mixture.

The allograft mixture includes non-demineralized cortical cancellous allograft granules or other suitable osteoconductive material, which may be fully contained by the mesh due to their physical size, and can thereby provide some structural strength to the bony defect. The granules provide a focus for load bearing or load sharing just as the pebbles in concrete. The ratio of cortical to cancellous allograft may be in the range of 25:75-100:0.

The granules may be mixed with DBM or other suitable osteoinductive material, which is a fine particulate, and a lubricating carrier. As the mesh is filled with the cortical cancellous allograft granules, some of the particulate DBM may be retained within the filled mesh, but a portion of it may be free to flow out through the pores of the mesh. This results in a surrounding "halo" of osteoinductive material at the margins of the filled mesh, in direct apposition with the surrounding host tissue where it can initiate recruitment of the stem cells, thus encouraging bone growth to heal the bony defect.

BRIEF DESCRIPTION OF THE FIGURES

The invention can be completely understood in consideration of the following detailed description of various embodiments of the invention in connection with the accompanying drawings, in which.

Figure 1:
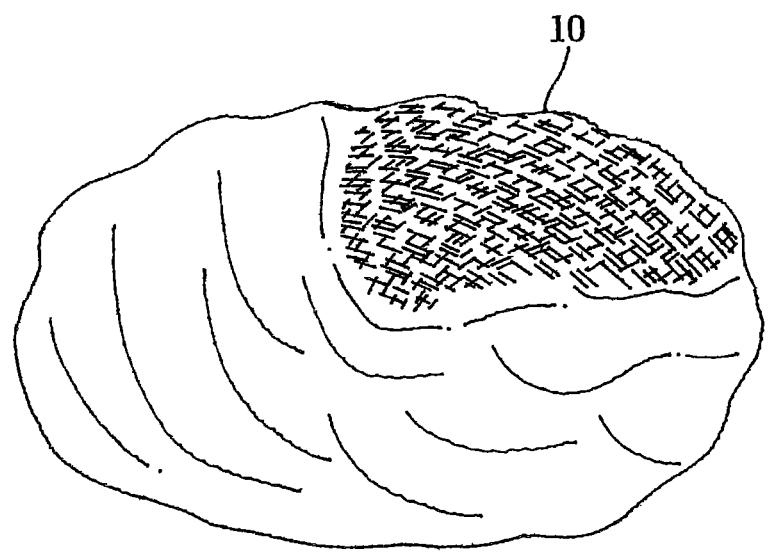
FIG. 1 is a representative side view of the distribution of DBM particles within a mesh container as the DBM particles are fed into the mesh container according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

The allograft mixture may generally be comprised of three components: non-demineralized cortical cancellous allograft granules or other suitable osteoconductive material, demineralized bone matrix ("DBM") or other suitable osteoinductive material and sodium hyaluronan (HA), or other suitable lubricating carrier. The non-demineralized cortical cancellous allograft granules may generally be 200-2000 microns in size and may have an aspect ratio of about 1.5 longer than wide. The DBM may generally be 100-1000 microns in size and tends to be more uniform and rounded in shape. The lubricating carrier may generally be a viscous liquid, for example, sodium hyaluronan in varying molecular weights, alginate, dextran, gelatin, collagen and others. The DBM is more likely than the non-demineralized granules to be suspended in the lubricating carrier due to the geometric and size difference between the DBM and the non-demineralized granules.

Ceramic materials may be added as alternatives to the cortical cancellous granules. The ceramics are also load bearing, load sharing, and osteoconductive. The ceramic material formulation may include, for example, calcium hydroxyapatite, tricalcium phosphate and calcium sulfate among others. Calcium hydroxyapatite resorbs very slowly, over a period of years. Tricalcium phosphate resorbs slowly, in about 3-6 months. Calcium sulfate resorbs more quickly, in less than 3 months.

As shown in FIG. 1, the tendency for the DBM to flow with the carrier is particularly noticeable when the mixture is delivered and packed into the mesh container 10. The DBM particles flow through the mesh pores under the force applied by the emptying of the filled tube into the confined mesh container. The smaller of the DBM particles flow through the mesh pores into the bony defect. These DBM particles are the sole osteoinductive elements in the mixture. As the DBM is forced through the mesh pores, the DBM makes intimate contact with the irregular surfaces of the bony defect and consequently causes new bone to grow precisely at the surfaces where bony fusion is intended.

The mesh pores, generally about 250-5000 microns, may act as a sieve or filter that preferentially retains the non-demineralized granules. This filtering feature may allow the larger, irregularly shaped granules to pack tightly together within the mesh while the fluid component, also carrying the particles of DBM, may fill the interstices of the packed granules and flow through the pores of the mesh.

The relationship between the sizes of the DBM, the mesh pores and the granules may generally be described as follows: If the granules have a size equal to X, then the DBM size may generally be in the range of 0.3-0.7X and the pore size may generally be in the range of 0.5-2.5X.

The formulation of the mixture may generally be in the range of about 2 parts DBM, 8 parts non-demineralized allograft granules and 8 parts lubricating carrier.

The non-demineralized granules are primarily osteoconductive (supporting bone growth on the surface, but not strongly inducing growth), while the DBM is both osteoconductive and osteoinductive (encourages bone to grow). Because the DBM is osteoinductive, as the DBM flows out of the mesh pores in the fluid carrier, the DBM creates an increased potential for bone growth surrounding the mesh container, at the host-mesh interface, which may help to speed bony healing, or incorporation of the mesh and graft into the host bone structure.

Figure 2:
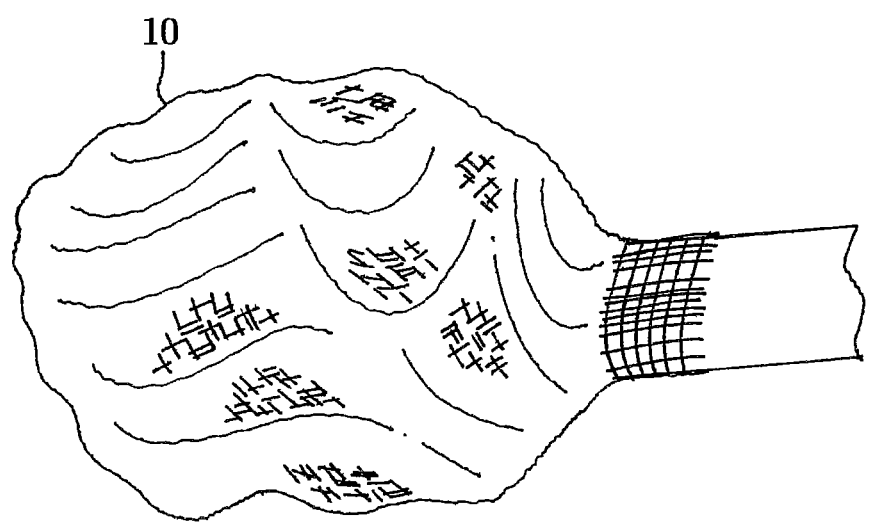
FIG. 2 is perspective view of a single porous mesh container for receiving a fill material mixture according to an embodiment of the present invention.

As shown in FIG. 2, a single mesh container 10 may have varying pore sizes, resulting in a differential porosity. That is, where the pores are larger, more fill material will flow out of the pores and where the pores are smaller less fill material will flow out of the pores. This differential porosity allows the surgeon to direct the flow of material out of the mesh pores and thus optimize the placement of the osteoinductive DBM more precisely to promote bony growth at the defect site.

Figure 3:
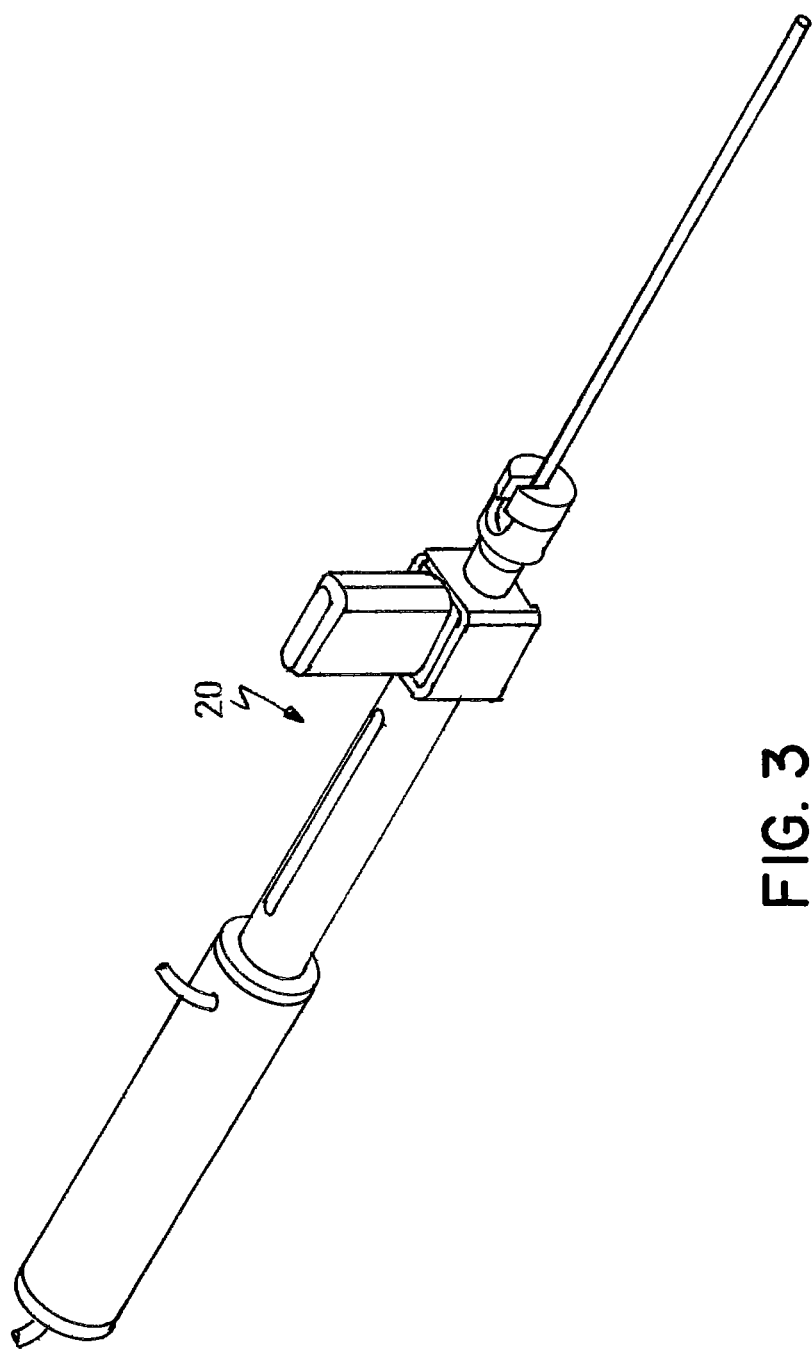
FIG. 3 is a perspective view of a tool for injecting a fill material mixture according to an embodiment of the present invention.
Figure 4:
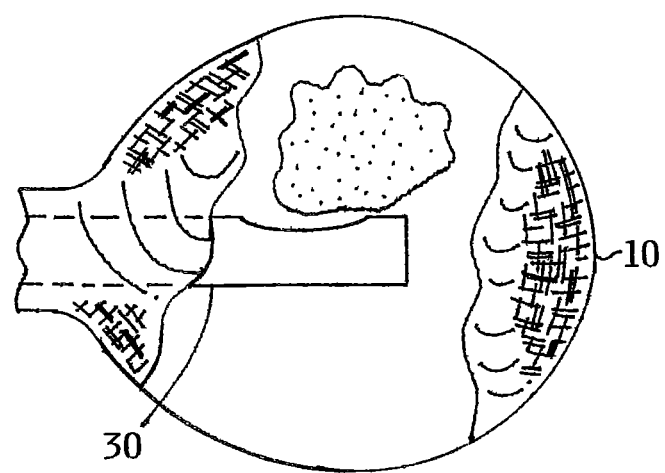
FIG. 4 is a representative cross-sectional side view of the extrusion of a fill material mixture into a porous container through a fill tube according to an embodiment of the present invention.

FIG. 3 shows a preferred tool 20, patented as U.S. Pat. No. 6,620,169 to Spineology, Inc, that may be used to process and inject the fill material mixture. In a preferred embodiment, the tool 20 shown in FIG. 3 is used to process the fill material mixture and inject the mixture into fill tubes. FIG. 4 shows the preferred embodiment where the fill material mixture is extruded from a fill tube 30 having at least one opening to direct the flow of the fill material mixture into the porous container 10 for optimal fill material placement.

Additional components, for example, bone morphogenic protein, vascular endothelial growth factor, platelet derived growth factor, insulin-like growth factor, chondrocyte growth factor, fibroblast growth factor, antiviral agents, antibiotic agents and others may be added to the formulation.

The invention claimed is:

1. A kit for treating bone comprising:
a fill material mixture including osteoconductive material, osteoinductive material and a lubricating carrier, the osteoconductive material having a particle size of 200 to 2000 microns, the osteoinductive material having a particle size about 60 to 1400 microns;
a porous container to receive the fill material mixture, the container having pore sizes about 100 to 5000 microns;
a tool that flowably introduces the fill material mixture into the porous container at sustained or intermittent pressures of at least 300 psi such that the fill material mixture is packed into the container;
and a halo layer of osteoinductive material at least 1 mm forms around at least a portion of an exterior surface of the porous container.

2. The device of claim 1 wherein the ratio of the fill material mixture is about 1 part osteoinductive material to 2 parts osteoconductive material to 2 parts lubricating carrier.

3. The device of claim 1 wherein the osteoinductive material is demineralized bone material.

4. The device of claim 1 wherein the osteoconductive material is selected from the group consisting of: cortical cancellous allograft, cortical cancellous autograft, cortico cancellous xenograft, hydroxyapatite, tricalcium phosphate, calcium sulfate, calcium carbonates and any combination thereof.

5. The device of claim 1 wherein the mixture is selected from a group consisting of: demineralized bone material, morselized bone graft, cortical cancellous allograft, cortical cancellous autograft, cortical cancellous xenograft, hydroxyapatite, tricalcium phosphate, calcium sulfate, calcium carbonates and any combination thereof.

6. A method of treating bone comprising the steps of:
inserting a porous container into a bony defect;
introducing the fill material mixture into the porous container at a pressure of at least 300 psi such that the fill material mixture is packed into the container forming a halo layer of osteoinductive material at least 1 mm around at least a portion of an exterior surface of the porous container.

7. The method of claim 6 wherein the ratio of the fill material mixture is about 1 part osteoinductive material to 2 parts osteoconductive material to 2 parts lubricating carrier.

8. The method of claim 6 wherein the particle size of the osteoconductive material is 200 to 2000 microns, the particle size of the osteoinductive material is about 60 to 1400 microns and the container pore sizes are about 100 to 5000 microns.

9. The method of claim 6 wherein the osteoinductive material is demineralized bone material.

10. The method of claim 6 wherein the osteoconductive material is selected from the group consisting of: cortical cancellous allograft, cortical cancellous autograft, cortico cancellous xenograft, hydroxyapatite, tricalcium phosphate, calcium sulfate, calcium carbonates and any combination thereof.

11. The method of claim 6 wherein the mixture is selected from a group consisting of: demineralized bone material, morselized bone graft, cortical cancellous allograft, cortical cancellous autograft, cortical cancellous xenograft, hydroxyapatite, tricalcium phosphate, calcium sulfate, calcium carbonates and any combination thereof.

* * * * *